United States Patent [19]

Shum et al.

[11] 4,121,989
[45] Oct. 24, 1978

[54] METHOD OF MAKING OXYGEN SENSOR

[75] Inventors: Ming S. Shum, Des Plaines; Roy E. Svacha, North Barrington; Kenneth R. Janowski, Wheaton, all of Ill.; Anthony V. Fraioli, East Selauket, N.Y.

[73] Assignee: UOP Inc., Des Plaines, Ill.

[21] Appl. No.: 856,825

[22] Filed: Dec. 2, 1977

Related U.S. Application Data

[62] Division of Ser. No. 775,078, Mar. 7, 1977.

[51] Int. Cl.$^2$ .................................................. G01N 27/46
[52] U.S. Cl. ........................... 204/195 S; 123/119 E; 427/125; 29/570
[58] Field of Search ........................ 204/15, 195 S; 123/119 E; 427/125; 29/570

[56] References Cited

U.S. PATENT DOCUMENTS

| | | | |
|---|---|---|---|
| 3,723,589 | 3/1973 | Kennedy | 29/570 |
| 3,767,469 | 10/1973 | Flais et al. | 204/195 S |
| 3,841,987 | 10/1974 | Friese et al. | 204/195 S |
| 3,935,089 | 1/1976 | Togawa et al. | 204/195 S |
| 3,940,327 | 2/1976 | Wagner | 204/195 S |
| 3,965,552 | 6/1976 | Rutt | 427/125 |
| 3,978,006 | 8/1976 | Topp et al. | 204/195 S |
| 4,040,929 | 8/1977 | Bauer | 204/195 S |
| 4,040,930 | 8/1977 | Dillon | 204/195 S |

Primary Examiner—T. Tung
Attorney, Agent, or Firm—James R. Hoatson, Jr.; Barry L. Clark; William H. Page, II

[57] ABSTRACT

Oxygen sensor specifically adapted for use in an industrial air/fuel control system provides an ability to measure actual oxygen content quantitatively in industrial situations where off-stoichiometric air/fuel control is desired. The sensor is quite simple and is easy to use since it provides accurate reproducible readings from sensor to sensor and for long periods. The leads to the solid electrolyte disc are of the same material as the electrodes and extend to the remote end of the sensor so as to eliminate dissimilar material junctions. Felted ceramic discs applied to the wet paste electrodes before firing serve to filter the gases contacting the sensor and act as wicks for permitting uniform dispersion of chloroplatinic acid to the paste electrodes.

2 Claims, 2 Drawing Figures

METHOD OF MAKING OXYGEN SENSOR

This is a division of application Ser. No. 775,078, filed Mar. 7, 1977.

BACKGROUND OF THE INVENTION

The invention relates to oxygen sensors and particularly to sensors for use in industrial air/fuel control systems.

Sensors to be included as parts of industrial air/fuel control systems must meet requirements peculiar to industrial air/fuel control. In general, air/fuel ratio control in an industrial system is done in the excess air regime. This is done to insure that complete combustion of the fuel occurs and that no visible smoke stack emissions are produced. A second beneficial reason for controlling in this region has been a demonstrated improvement in combustion efficiency and resultant lowered fuel consumption.

In order that a sensor meet these requirements and still be commercially feasible, sensor performance must meet a number of criteria not normally significant for many other sensor applications. For example, sensor-to-sensor reproducibility is important. Without this demonstrated reproducibility, control system recalibration would be required at the time of each sensor replacement. Stability of the sensor signal over long term usage is also an extremely important feature, so that frequent system recalibration is not necessary. Another feature which is important in an industrial application is simplicity of installation of the sensor into the gaseous environment which is being measured. Finally, low sensor cost is important, particularly when replacement of sensors may be necessary.

The application of oxygen measuring sensors as either simple monitors of oxygen content or as sensors in control systems has received considerable interest in the patent literature. The earliest commercial application of oxygen sensing devices was as integral components in systems designed for measuring dissolved oxygen in molten metal baths. This area is still of considerable commercial importance as indicated by a number of recent patents in this area including U.S. Pat. Nos. 3,359,188 by Fischer, 3,378,478 by Kolodney, 3,403,090 by Tajiri and 3,791,954 by Noda. The devices covered in these patents are all similar in that they are solid electrolytic sensors which are immersed in a liquid metal and which generate an electrical signal which is a function of the oxygen content of the metal. The first three devices incorporate closed ended tubes of the electrolytic material while the fourth sensor uses a disc of solid electrolyte sealed into a retaining tube.

Most of the sensing devices utilized for measuring the oxygen content in molten metals are marketed as destructable sensors, in that they react with the molten metal being measured and are consumed in the course of the measurement. In U.S. Pat. No. 3,297,551 by Alcock a liquid metal sensor is presented which is used in the liquid metal heat exchanger of a nuclear reactor on a long term continuing basis.

Other sensors have been designed for measuring oxygen content specifically in gaseous mixtures rather than in liquid metals. For example, U.S. Pat. No. 3,974,054 by Poolman covers a disc electrolyte bonded to an aluminum oxide tube which is used for determining oxygen concentrations in gaseous mixtures. Another gas sensor is presented in U.S. Pat. No. 3,989,614 by Tien which specifies a sensor composed of a tubular solid electrolyte. In addition to the above, a number of oxygen sensors and sensing systems are commercially available, all of which use solid electrolytic sensing of oxygen.

Recently, there has been a considerable amount of interest in the measurement of the components which make up automotive exhaust gases. A number of devices have been patented for the measurement of the stoichiometric air/fuel ratio going into internal combustion engines. These are proposed to be used with control systems to hold engine operating conditions at the stoichiometric value. Proposed devices include both those that work as electrical resistance sensing elements as well as electrolytic sensors.

Typical resistance sensors have been covered in U.S. Pat. Nos. 3,911,386 by Beaudoin; 3,936,794 by Beaudoin and 3,959,765 by Stewart. These devices sense a change in the electrical resistance of ceramic elements which show a change in electrical resistance that can be correlated with ambient oxygen pressure.

Of greater interest, however, are those automotive oxygen sensors which operate on electrolytic principles. A number of patents have been issued in this area on sensors which have the electrolyte in the form of tubes or discs.

Tube sensor patents include British Pat. No. 1,385,464 by Bosch and U.S. Pat. Nos. 3,841,987 by Friese; 3,935,089 by Togawa; 3,960,693 by Weyl, and 3,978,006 by Topp. All of these patents specify automotive oxygen sensors where the solid electrolyte is in the form of an open-ended tube, the open end being in communication with the ambient air environment.

The disadvantages inherent in such tubular electrolytic sensors have led to the development of simplified automotive oxygen sensors incorporating electrolyte discs rather than tubes. The disadvantages of the tubular sensors include complexity and the resultant cost in producing the electrolyte tube, and the expense and difficulty involved in applying large amounts of costly electrode materials over the surface of the tube.

The development of sensors incorporating very simple electrolytic discs has circumvented these problem areas. Examples of such automotive oxygen sensors incorporating discs include U.S. Pat. Nos. 3,819,500 by VanEsdonk; 3,909,385 by Spielberg; 3,768,259 by Carnahan, and 3,940,327 by Wagner.

There are a number of disadvantages in applying either currently available industrial or automotive sensors to feedback control systems designed for use in industrial combustion control. Those sensors specifically designed for industrial use are generally of a large size are costly to replace, operate at high temperatures which limits useful life, or are designed to be used only once. In addition, those industrial sensors constructed with tubular electrolytes suffer the same disadvantage as tubular automotive sensors, that is high electrolyte cost and the necessity for relatively large electrodes made of expensive materials. Those industrial sensors commercially available generally operate at about 1500° F. Continuous operation at this temperature causes deterioration of the electrode which seriously affects performance as well as thermal fatigue in the electrolyte when it is subjected to heating cycles.

Likewise, the application of sensors designed for automotive use to industrial air/fuel control has not generally been successful. Sensor-to-sensor reproducibility of sufficient accuracy has not been demonstrated with this type of sensor to be useful in controlling a specific oxygen content far from the stoichiometric value. In general, these automotive sensors have been designed as indicators only of the stoichiometric air/fuel ratio, rather than sensors which measure actual oxygen content quantitatively. They have also been designed to survive in the severe automotive environment. This design is not necessary for industrial air/fuel applications and results in a considerable unnecessary increase in cost and design complexity.

One problem which all of the automotive sensors seem to share is the introduction of undesirable electrical signals due to dissimilar material junctions. While this is not a problem in sensors used for stoichiometric air/fuel ratio definition, such signals can have extremely deleterious effects on sensors which are being used to quantitatively measure oxygen content, such as is necessary in off-stoichiometric air/fuel control in industrial applications.

SUMMARY

It is the object of the present invention to provide an industrial air/fuel sensing device which eliminates the aforementioned problems.

The proposed design incorporates features common to most of the sensors in the patents cited hereinabove, in that it is a solid electrolytic oxygen ion conducting cell with noble metal electrodes. The electrolyte is in the form of a disc and shares the advantages of the cited industrial and automotive disc sensors when compared to the tubular varieties of these sensors. It is much simpler in design, however, than other sensors and, most importantly, the novel features of this design have been incorporated so that it can be used in industrial air/fuel control systems without the disadvantages of other designs.

The electrolyte disc is preferably $ZrO_2$-8 mole % $Y_2O_3$. This disc is sealed into the recessed end of a fabricated forsterite tube, using glass, such as Corning 1415, as a sealant. The forsterite tube is machined prior to firing to produce a retaining shoulder, a recess into which the electrolyte disc is sealed, and two grooves on the opposite end of the tube. The recess is machined to a depth greater than necessary to accept the electrolyte disc. The reason for this extra recess will be discussed below.

After sealing the disc into the tube, a commercially available fluxed platinum paste, such as Plessey 4276, is deposited on the two exposed surfaces of the disc. In addition, one platinum paste stripe is painted along the inside diameter of the forsterite tube, over the end and into the bottom recessed groove on the outside diameter of the tube. A second stripe is painted from the top surface of the disc along the tube outside diameter to the upper groove. While the platinum paste electrodes are still tacky, felted ceramic fiber discs are pressed into the paste on both electrodes.

The felted ceramic fiber material can be obtained from Cotronics Corp. of New York City as No. 300 ceramic paper and serves a number of functions. During operation of the sensing device, it acts as a combination filter to remove particulate matter and gaseous poisons from the stack gas being measured and a barrier to protect the electrode from any gaseous erosion that might occur. Another important function of the ceramic fiber disc is its role as a wick during application of chloroplatinic acid (hereinafter CPA) to be discussed below. The open fiber structure of the ceramic fiber disc allows uniform deposition of the CPA on the paste substrate. The importance of this deposition will also be discussed below. A fiber disc thickness of about 0.040 inches has proved to be quite satisfactory.

The openness of the felted material is important in the operation of the device for industrial applications due to the relatively slow gas flow rate often inherent in such applications. Experiments conducted substituting a more dense material such as gamma-alumina for the felted ceramic disc were not successful due to the inability of the gas to penetrate through the layer and reach the electrode material where oxygen ionization occurs.

Our application technique involves pressing the felted fiber disc into the tacky Pt paste and then firing in a furnace at 1750° F. in air for 30 minutes to cure the platinum paste and firmly bond the two ceramic fiber discs to the platinum paste. So bonded they will remain in place during the operation of the sensor in the industrial application.

Chloroplatinic acid is then applied through the ceramic fiber discs directly onto the surface of the platinum paste substrate. Sufficient CPA is applied to insure adequate coverage of the platinum paste substrate. This requires about 0.5 mg of platinum or about 0.01 ml of CPA per sensor where the electrolyte disc has a diameter of about 0.388 inches and a thickness of about 0.060 inches. The amount required is low due to the small area of the electrolyte and the efficient wicking action of the felted disc. Ionization of the oxygen in the stack gas environment takes place at the surface of the electrolyte, in the presence of both the platinum deposited as the paste substrate and high surface Pt from the CPA. If sufficient platinum surface is not present on the faces of the electrolyte disc, as would be the case if only platinum paste were present, ionization of residual oxygen would not be complete, and non-reproducible sensor performance would result. It is important that both surfaces of the electrolyte disc have sufficient platinum surface area present to complete the ionization-deionization reactions which occur on these surfaces. Therefore, sufficient CPA must be added to both the gas and reference sides of the electrolyte.

The purpose in bringing both the front and back conducting stripes to separate grooves fabricated in the forsterite tube is to insure the elimination of the dissimilar material junctions. Such junctions have been shown to introduce irreproducible and unwanted signals onto the true, theoretically predictable cell output. While not important in stoichiometric sensors, this feature is critical in importance for non-stoichiometric industrial control. By bringing all of these junctions out of the cell, these unwanted voltages can be eliminated and sensor reproducibility and stability insured if the other sensor features discussed above are included.

The purpose of the extra deep recess in the electrolyte end of the forsterite tube is to assist in eliminating the erosion effects of a flowing gas stream. In addition, this recess promotes turbulence in the stream at the sensor electrolyte location and allows continuous interaction of the stack gas with the electrolyte, assuring gaseous measurements are valid representations of the gas stream.

The final assembly operations include painting a gasket material such as graphite paste onto the forsterite tube at the locating shoulder or flange and compressing this gasket material between the metal body and the pressure nut. Alternatively, the forsterite tube can be produced without the locating ring and a compression gland can be used for sealing. This would simplify the design even further, thereby reducing costs.

The advantages of our improved sensor are the following: (1) it is simple; (2) uses very few parts; (3) the amount of platinum used is very small; (4) it is accurate and reproducible so that it can be used in industrial applications to indicate true oxygen content; (5) all dissimilar material junctions have been eliminated; and (6) the sensor has demonstrated long term operation at 1300° F. lower than the 1500° F. operating temperature of other industrial sensors. This relatively low operating temperature in an industrial environment is a marked improvement over currently available commercial sensors. In addition, it has been shown that the installation of this sensor directly into stack gas systems can be done very simply compared to other available sensors.

DESCRIPTION OF THE PREFERRED EMBODIMENT

Figure 1:
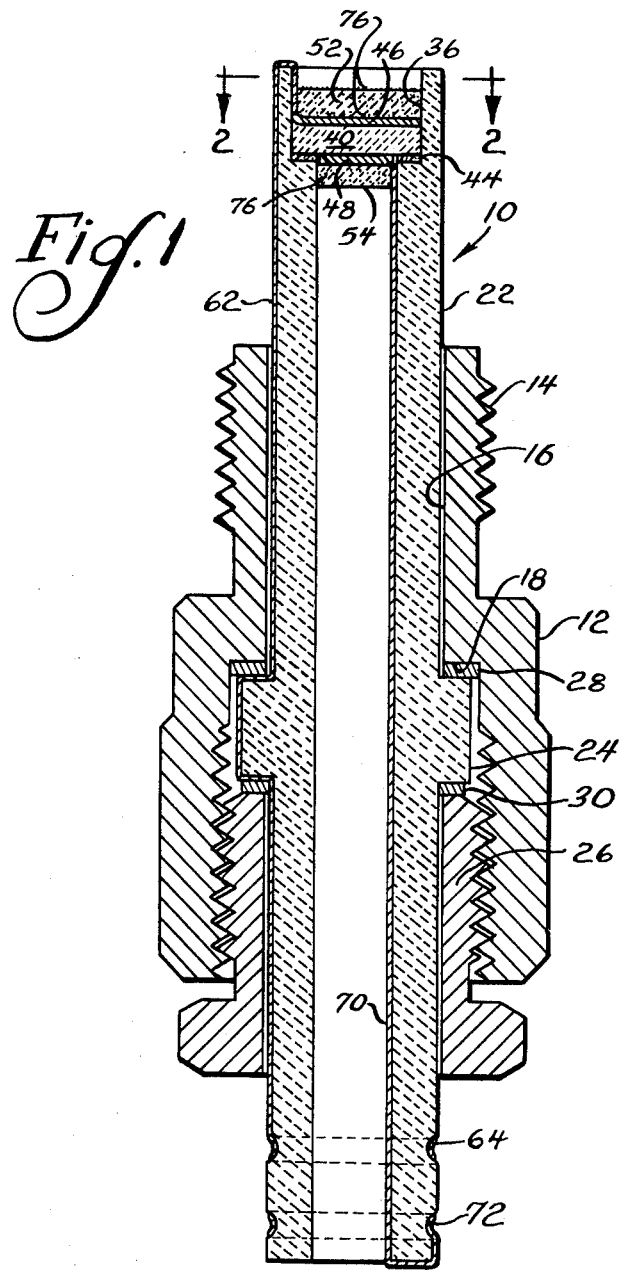
FIG. 1 is a side sectional view of the improved sensor taken on its axis.
Figure 2:
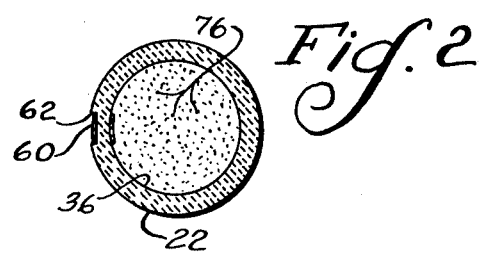
FIG. 2 is an end sectional view taken on line 2—2 of FIG. 1.

Referring to the drawings, our improved sensor indicated generally at 10 comprises a generally tubular metal body member 12 which is preferably made of a corrosion-resistant material such as stainless steel. The body 12 includes means such as integral threads 14 for attaching the sensor to the wall of a flue gas containing conduit such as a smoke stack. The interior of the body member 12 includes an inner wall portion 16 and a recessed shoulder portion 18. An electrical insulating ceramic tube 22 made of a material such as forsterite includes an integral flange or annular ring portion 24 which comprises a retaining means which cooperates with the recessed shoulder retaining means 18 in the body 12 to restrict upward movement of the tube 22 relative to the body. A pressure nut 26 which is threadably engaged with the body 12 prevents a downward movement of the tube 22 and cooperates with the graphite gasket members 28, 30 to mount the tube 22 in fixed gas-tight relation to the body 12. The upper or sensing end of the ceramic tube 22 is recessed at 36 to accommodate the oxygen ion conducting solid electrolyte disc 40 which is mounted in the recess by means of a glass seal 44. The front or sensing electrode 46 and a rear reference electrode 48 are preferably applied to the electrolyte 40 in the form of a platinum paste. Prior to firing, and while the paste electrodes 46, 48 are still wet, felted ceramic front disc member 52 and a felted ceramic rear disc member 54 are pressed into them. An outer conductive lead member 60, which is preferably formed of the same platinum paste material as the electrodes, is painted on the surface of tube 22 so as to extend from the sensing electrode 46, which it contacts, around the upper end of the tube and down the length of its outer side in a shallow groove 62 until it is terminated in an upper annular groove 64 which may be contacted by appropriate instrumentation (not shown). The purpose of the groove 62 is to protect the very thin lead member 60 from damage or breakage as the tube 22 is handled or inserted into the housing 12. An inner platinum paste lead member 70 is painted into electrical contact with the reference electrode surface 48 and down the inside surface of the tube 22, around its lower end, and into a lower annular groove 72 which may be connected into an electrical circuit (not shown). The painted lead members 60, 70 are, of course, painted into contact with the electrodes 46, 48 before the ceramic filter discs 52, 54 are attached by pressing them into contact with the wet paste electrodes. Then, the entire tube 22 is fired in air at 1850° F. for about 15 minutes. Then, the electrodes 46, 48 are impregnated with a platinum group metal component from a solution of a soluble precursor compound thereof which is applied to the filter discs 52, 54 and then fired at conditions to effect the reduction of the platinum group metal component. Preferably, the solution is CPA and the reduction is accomplished by heating the tube assembly in hydrogen for about 30 minutes to a temperature of 850° F., holding the assembly at 850° F. in hydrogen for about 60 minutes, and cooling the assembly down in an atmosphere of nitrogen. The reduced platinum particles 76 are uniformly dispersed over the electrode surfaces 46, 48.

We claim as our invention:

1. A method of making an oxygen sensor comprising the steps of taking a pre-fired non-electrically conducting hollow ceramic tube and forming a reduced diameter recess in the inner or sensing end thereof; placing a coating of glass sealing material at the bottom of the recess; applying a coating of a platinum paste electrode to each side of a disc of an oxygen ion conducting solid electrolyte; placing said electrolyte disc in said recess with its outer reference surface in contact with said glass sealing material; applying a stripe of platinum paste to the outer reference electrode on said disc and along the internal surface of the tube to the outer or reference end thereof; applying a stripe of platinum paste to the inner sensing electrode on said disc, around the inner end of said ceramic tube and along the outer surface thereof to a location adjacent the reference end of said tube; pressing a ceramic fiber filter disc into the platinum paste electrodes on each side of said electrolyte disc; firing said tube in air at a temperature of at least about 1850° F.; and impregnating said electrodes with a platinum group metal component from a solution of a soluble precursor compound thereof applied to said filters and then firing at conditions to effect the reduction of said platinum group metal component.

2. The method of claim 1 wherein said electrodes are impregnated with platinum from a solution of chloroplatinic acid.

* * * * *